United States Patent
Grodzki et al.

(10) Patent No.: US 9,101,659 B2
(45) Date of Patent: Aug. 11, 2015

(54) METHOD AND APPARATUS FOR CORRECTION OF ARTIFACTS IN MAGNETIC RESONANCE IMAGES

(71) Applicants: David Grodzki, Erlangen (DE); Bjoern Heismann, Erlangen (DE)

(72) Inventors: David Grodzki, Erlangen (DE); Bjoern Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 192 days.

(21) Appl. No.: 13/656,932

(22) Filed: Oct. 22, 2012

(65) Prior Publication Data

US 2013/0101198 A1   Apr. 25, 2013

(30) Foreign Application Priority Data

Oct. 21, 2011   (DE) .......................... 10 2011 085 033

(51) Int. Cl.
 *G06K 9/00* (2006.01)
 *A61K 48/00* (2006.01)
 *G01R 33/48* (2006.01)
 *G01R 33/565* (2006.01)
 *G06F 17/16* (2006.01)

(52) U.S. Cl.
 CPC ................ *A61K 48/00* (2013.01); *G01R 33/48* (2013.01); *G01R 33/4816* (2013.01); *G01R 33/565* (2013.01); *G06F 17/16* (2013.01)

(58) Field of Classification Search
 None
 See application file for complete search history.

(56) References Cited

U.S. PATENT DOCUMENTS

| 2005/0001619 A1* | 1/2005 | Kiefer | 324/309 |
| 2008/0021304 A1* | 1/2008 | Stemmer | 600/410 |
| 2010/0244827 A1* | 9/2010 | Hennel | 324/309 |
| 2010/0277172 A1* | 11/2010 | Takizawa | 324/309 |
| 2011/0105884 A1* | 5/2011 | Beck | 600/410 |

OTHER PUBLICATIONS

3D Radial Projection Technique With Ultrashort Echo Times for Sodium MRI: Clinical Applications in Human Brain and Skeletal Muscle, Nielles-Vallespin et al., Magnetic Resonance in Medicine vol. 47, pp. 74-81 (2007).
Ultra short Echo Time Imaging using Pointwise Encoding Time reduction with Radial Acquisition (PETRA), Grodzki et al., Proc. Intl. Soc. Mag. Reson. Med. vol. 19, p. 2815 (2011).
MRI with Zero Echo Time: Hard versus Sweep Pulse Excitation, Weiger et al., Magnetic Resonance in Medicine vol. 66, pp. 379-389 (2011).
Signal decay correction in 2D ultra-short echo time imaging, Mentrup et al., Magn. Reson Mater Phy vol. 19, pp. 62-70 (2006).
Analytic reconstructionof amgnetic resonance imaging signal obtained from a periodic encoding field, Rybicki et al., Med. Phys. vol. 27, pp. 2060-2064 (2000).

* cited by examiner

*Primary Examiner* — Amara Abdi
(74) *Attorney, Agent, or Firm* — Schiff Hardin LLP (57) ABSTRACT

In a method and apparatus for the correction of artifacts in magnetic resonance images (MR) acquired with an MR pulse sequence in which gradients are switched simultaneously during the radiation of at least one non-selective excitation pulse, measurement data acquired with the pulse sequence in k-space are loaded into a processor, in which a perturbation matrix is determined on the basis of spatial and k-space point data of the acquired measurement data and the gradients used during the excitation. A corrected image is calculated from the acquired measurement data in k-space and the perturbation matrix, with the calculation of the corrected image including a matrix inversion of the perturbation matrix. The corrected image is then stored or displayed.

11 Claims, 4 Drawing Sheets

METHOD AND APPARATUS FOR CORRECTION OF ARTIFACTS IN MAGNETIC RESONANCE IMAGES

BACKGROUND OF THE INVENTION

1. Field of the Invention

The invention concerns: a method to correct artifacts in magnetic resonance (MR) images by means of an MR pulse sequence in which gradients are switched (activated) simultaneously during the radiation of at least one excitation pulse, as well as a magnetic resonance apparatus and an electronically readable data medium for implementing such a method.

2. Description of the Prior Art

The magnetic resonance modality (also known as magnetic resonance tomography) is a known technique with which images of the inside of an examination subject can be generated. Expressed simply, for this purpose the examination subject is positioned within a strong, static, homogeneous basic magnetic field (also called a $B_0$ field) having a field strength of 0.2 Tesla to 7 Tesla and more, such that the nuclear spins of the examination subject are oriented along the basic magnetic field. To trigger nuclear magnetic resonance signals, radio-frequency excitation pulses (RF pulses) are radiated into the examination subject, the triggered magnetic resonance signals are measured (detected) in a form known as k-space data, and MR images are reconstructed, or spectroscopy data are determined, based on these nuclear magnetic resonance signals. For spatial coding of the measurement data, rapidly switched magnetic gradient fields (also shortened to "gradients") are superimposed on the basic magnetic field. The acquired measurement data are digitized and stored as complex numerical values in a k-space matrix. An associated MR image can be reconstructed from the k-space matrix populated with such values, for example by means of a multidimensional Fourier transformation.

Sequences with very short echo times TE, for instance TE less than 0.5 milliseconds, offer new fields of application for magnetic resonance tomography. They enable the depiction of substances that cannot be shown with conventional sequences such as (T)SE ((Turbo)Spin Echo) or GRE (Gradient Echo), since the respective decay time of the transverse magnetization T2 in such ultrashort sequences is markedly shorter than the possible echo times of the conventional sequences, which means that in the conventional sequences the detectable signal has already decayed at the acquisition point in time. In contrast, with echo times in the same time range of these decay times, it is possible to show the signals of these substances, for example in an MR image. The decay times T2 of teeth, bones or ice lie between 30 and 80 microseconds, for example.

The application of sequences with ultra-short echo times (UEZ sequences) thus enables bone and/or teeth imaging and/or the depiction of cryo-ablations by means of MR, for example, and can be used for MR-PET (combination of MR and positron emission tomography, PET) or PET attenuation correction.

Examples of UEZ sequences are UTE ("Ultrashort Echo Time"), for example as it is described in the article by Sonia Nielles-Vallespin, "3D radial projection technique with ultrashort echo times for sodium MRI: Clinical applications in human brain and skeletal muscle", Magn. Res. Med. 2007; 57; P. 74-81; PETRA ("Pointwise Encoding Time reduction with Radial Acquisition") as is described by Grodzki et al. in "Ultra short Echo Time Imaging using Pointwise Encoding Time reduction with Radial Acquisition (PETRA)", Proc. Intl. Soc. Mag. Reson. Med. 19 (2011) P. 2815; or z-TE as is described by Weiger et al. in "MRI with zero echo time: hard versus sweep pulse excitation", Magn. Reson. Med. 66 (2011) P. 379-389.

Generally, in these sequences, a hard delta pulse is applied as a radio-frequency excitation pulse, and the data acquisition is subsequently started. In PETRA or z-TE, the gradients are already activated during the excitation. The spectral profile of the excitation pulse corresponds approximately to a sinc function. In the case of insufficient pulse bandwidth or gradients that are too strong, it may be that the outer image regions are no longer sufficiently excited.

In the reconstructed MR image, this incorrect excitation has the effect of blurring artifacts at the image edge, which are pronounced more strongly the stronger the gradients switched during the excitation.

An insufficient excitation thus leads to artifact-plagued MR images. This problem has previously for the most part been ignored. At best it is attempted to optimally reduce the strength of the gradients. However, imaging-relevant variables such as the readout bandwidth, the repetition time TR and the contrast of the image therefore change. For example, a reduction of the gradient strength increases the minimum necessary repetition time TR, and therefore also the total measurement time. Furthermore, such artifacts could be avoided in that the excitation pulses are selected to be particularly short in order to increase the excitation width. However, at the same time the maximum possible flip angle and the precision of the actually sent RF excitation pulse are therefore proportional to the duration of the RF excitation pulse. For example, given a duration of the excitation pulse of 14 microseconds the maximum flip angle amounts to approximately 9°, and given a reduced duration of the excitation pulse to 7 microseconds the maximum flip angle would amount to only approximately 4.5°. This procedure therefore also cannot be used without limitations and is accompanied by a degradation of the image quality.

SUMMARY OF THE INVENTION

An object of the present invention is to provide a magnetic resonance system, method and an electronically readable data storage medium that allow a reduction of artifacts in MR measurement with gradients switched during the excitation, without limiting the MR measurement.

The method according to the invention for the correction of artifacts in magnetic resonance images, which images were acquired by means of an MR pulse sequence in which gradients are switched simultaneously during the radiation of at least one non-selective excitation pulse, includes the steps of acquiring load measurement data acquired with the pulse sequence in k-space, determining a perturbation matrix on the basis of spatial and k-space point data of the acquired measurement data and the gradients used during the excitation, calculating a corrected image from the acquired measurement data in k-space and the perturbation matrix wherein the calculation of the corrected image includes a matrix inversion of the perturbation matrix, and displaying and/or storing the corrected image.

By the calculation of a perturbation matrix on the basis of the location to be measured, the read-out k-space points and the gradients applied during the excitation, and the inversion of this perturbation matrix, the interfering influence of a non-uniform, incorrect excitation can be remedied in a simple manner. The image quality can thus be markedly improved, primarily in the outer regions of the reconstructed image. In particular, a high homogeneity in the image and a sharp contrast can be achieved without artifacts. The strength of the applied gradients is not subjected to any limitations by the method according to the invention. This means that stronger gradients can also be switched without having to accept losses in the image quality. Longer lasting excitation pulses—and therefore higher flip angles—can likewise also be used with the method according to the invention, without negatively affecting the image quality.

The invention is based on the following considerations.

In measurements with gradients switched during the excitation, the excited region changes with each repetition because different gradient configurations are switched in each repetition. This leads to perturbations since, for example, with a repetition with a gradient configuration of Gx=0 and Gy=G, an image resulting from this measurement point is respectively overlaid with a sinc function corresponding to the incorrect excitation (the sinc function being symmetrical in the y-direction). In contrast, in the case of a repetition with a gradient configuration of Gx=G and Gy=0, for example, an image resulting from this measurement point is overlaid with a sinc function corresponding to the incorrect excitation (which sinc function is symmetrical in the x-direction).

Figure 1:
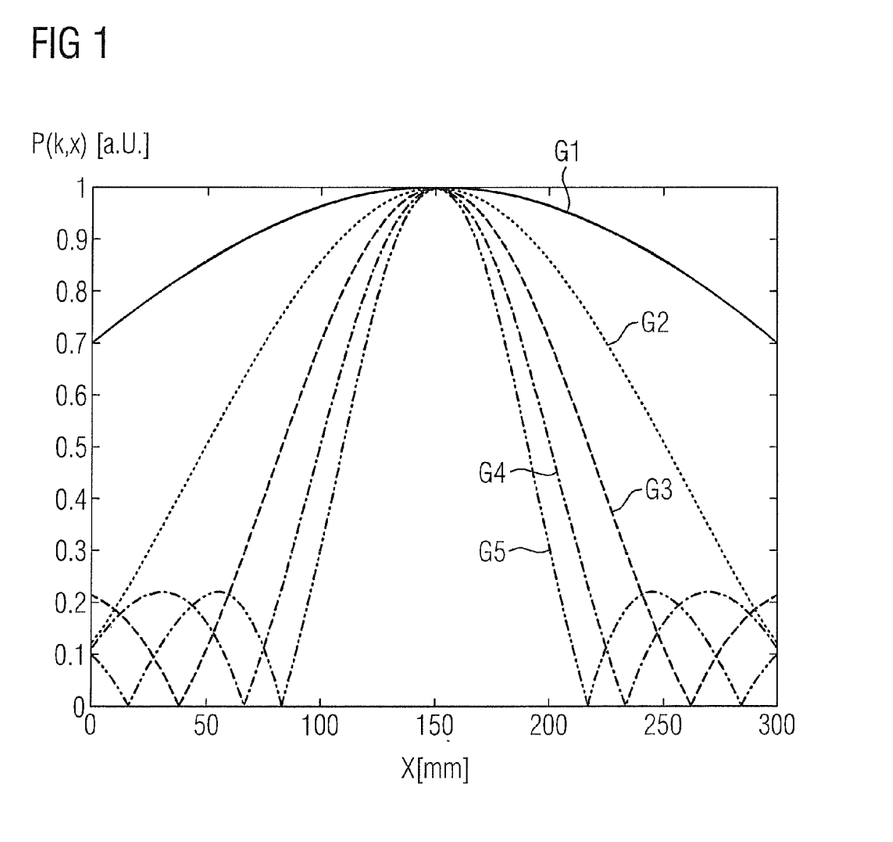
FIG. 1 shows the influence of the applied gradient strength on the excitation profile of an excitation pulse.

The dependency of the excitation profile in the x-direction (specified in millimeters "mm")—and therefore of the produced effect P(k,x) (specified in arbitrary units "a.U.")—on a currently applied gradient strength G1, G2, G3, G4, G5 is presented as an example in FIG. 1. In the shown example, G5>G4>G3>G2>G1. As is apparent, the excitation profile becomes wider as the applied gradient strength becomes smaller. The widest excitation profile (drawn with solid line)—i.e. an optimally homogenous excitation (P(k,x)) over the largest possible region (x)—is therefore achieved at G1. The narrowest excitation profile (drawn with double dash-dot line)—which already entails a drastic change in the excitation (P(k,x)) given a small spatial change (x)—is achieved at G5.

The problem can be described mathematically as follows. In MR measurements, what is known as k-space F(k) which corresponds to the examination region of the measured subject that is to be imaged is scanned, wherein:

$$F(k)=\int f(x)e^{ikx}dx. \quad (1)$$

wherein f(x) describes the signal of the subject to be measured, a k-space F(k) is filled with the acquired measurement data. The image I(x) is calculated by Fourier back-transformation from k-space filled with the measurement data:

$$I(x)=f(x)=\int F(k)e^{-ikx}dk. \quad (2)$$

In the case of insufficient excitation, instead of desired k-space F(k) distorted k-space F'(k) is measured, i.e. filled with the measurement data. In distorted k-space F'(k), the signal of the subject f(x) to be measured is overlaid with a perturbation function P(k,x) which corresponds to the spectral shape of the actual excitation pulse, thus the excitation profile:

$$F'(k)=\int f(x)P(k,x)e^{ikx}dx. \quad (3)$$

The excitation profile P(k,x) depends both on the location x and on the measured k-space point k and on the gradient strength. The excitation profile of an excitation pulse essentially corresponds to the Fourier transform of the pulse shape of the excitation pulse in time period p(t); in the example shown using FIG. 1, the excitation profiles correspond to a respective sinc function, for example as they result given "hard", rectangular excitation pulses p(t) which have a constant value (B1, for example) not equal to zero during the duration τ of the excitation pulse: A rectangular excitation pulse $$p(t) = \begin{cases} B1, & \text{for } |t| < \tau/2 \\ 0, & \text{otherwise} \end{cases}$$

corresponds in frequency space to a sinc-shaped spectral excitation profile P(w) with $$P(\omega) = \frac{\sin\left(\frac{1}{2}\omega\tau\right)}{\frac{1}{2}\omega\tau} = \text{sinc}\left(\frac{1}{2}\omega\tau\right) \text{ and a phase factor.}$$

In the presence of switched gradients, the resonance frequency ω is a function of the location (represented here by x) in the image domain: ω=2πγxG, with γ the gyromagnetic ratio and G the strength of the applied gradient. Given gradients varying in the course of the MR pulse sequence (for example in different repetitions), ω is also a function of the read-out k-space point k, which is why the excitation pulse can be written as P(ω)=P(k,x).

A distorted MR image I'(x) plagued with artifacts can be reconstructed from distorted k-space F'(k):

$$I'(x)=\int F'(k)e^{-ikx}dk. \quad (4)$$

According to the invention, the distorting influence of the incorrect excitation pulse is eliminated from the measured measurement data in that the excitation error is calculated in a perturbation matrix $D_{kx}$, and the error of the excitation is subsequently remedied via inversion of the perturbation matrix $D_{kx}$.

If Equation (3) is written as a sum (discrete values are actually measured) and if the perturbation matrix $$D_{kx}=P(k,x)e^{ikx} \quad (5)$$

is defined with N×N elements (wherein N is a natural number), Equation (3) can be written in matrix form:

$$F'_k=D_{kx}f_x. \quad (6)$$

The perturbation matrix $D_{kx}$ thus reproduces an excitation profile of the excitation pulse used to acquire the measurement data. The elements of Equation (5) are known and can be calculated from the shape of the excitation pulse, the location x to be excited and read-out k-space point k, as well as the applied gradients G. The distorted k-space F'(k) is measured. The undistorted image I(x) can therefore be calculated via matrix inversion of $D_{kx}$ and matrix multiplication with distorted k-space:

$$f_x=I_x=D_{kx}^{-1}F'_k. \quad (7)$$

The calculation of a corrected image $I_x$ (x) comprises a matrix multiplication of the perturbation matrix $D_{kx}^{-1}$ inverted via the matrix inversion with the measurement data acquired in k-space F'x.

A magnetic resonance system according to the invention comprises a basic field magnet; a gradient field system; a radio-frequency antenna; a control device to control the gradient field system and the radio-frequency antenna; and an image computer to receive measurement signals acquired by the radio-frequency antenna, to evaluate the measurement signals, and to create magnetic resonance images, and is designed to implement the method described herein.

The present invention also encompasses a non-transitory, computer-readable data storage medium encoded with programming instructions that, when the storage medium is loaded into a processor, cause the processor to implement one or more of the embodiments of the method according to the invention described above.

The advantages and embodiments described with regard to the method analogously apply to the magnetic resonance system, and the electronically readable data medium.

DESCRIPTION OF THE PREFERRED EMBODIMENTS

Figure 2:
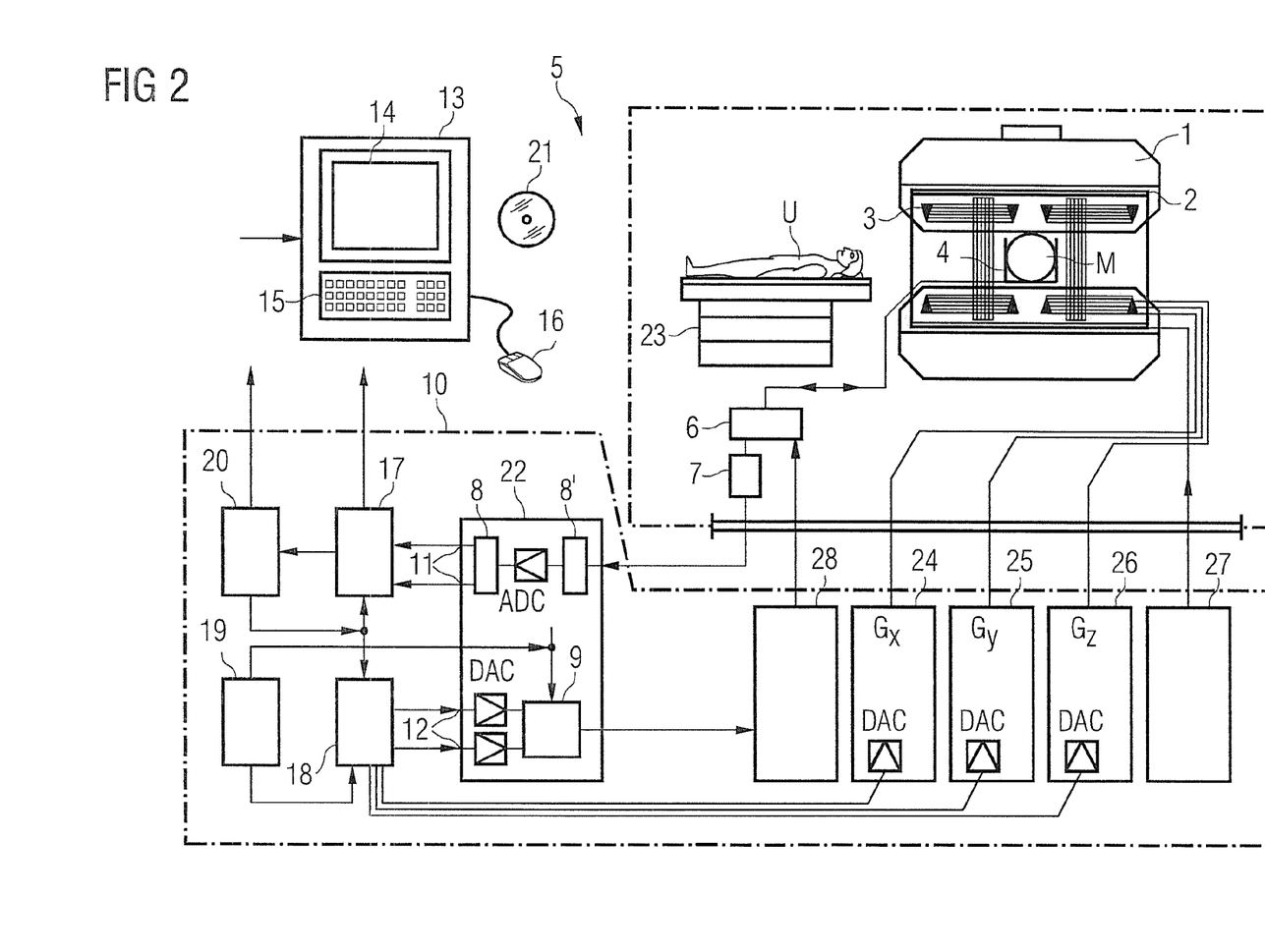
FIG. 2 schematically illustrates a magnetic resonance system according to the invention.

FIG. 2 schematically illustrates a magnetic resonance system 5 (a magnetic resonance imaging or magnetic resonance tomography apparatus). A basic field magnet 1 generates a temporally constant, strong magnetic field for polarization or alignment of the nuclear spins in an examination region of an examination subject U, for example of a part of a human body that is to be examined, which part lies on a table 23 and is moved into the magnetic resonance system 5. The high homogeneity of the basic magnetic field that is required for the magnetic resonance measurement is defined in a typically spherical measurement volume M into which the parts of the human body that are to be examined are introduced. To support the homogeneity requirements, and in particular to eliminate temporally variable influences, shim plates made of ferromagnetic material are mounted at a suitable point. Temporally variable influences are eliminated via shim coils 2 and a suitable controller 27 for the shim coils 2.

A cylindrical gradient coil system 3 that has three sub-windings is used in the basic field magnet 1. Each sub-winding is supplied by a corresponding amplifier 24-26 with current to generate a linear gradient field in the respective direction of a Cartesian coordinate system. The first sub-winding of the gradient field system 3 thereby generates a gradient $G_x$ in the x-direction; the second sub-winding generates a gradient $G_y$ in the y-direction; and the third sub-winding generates a gradient G, in the z-direction. The amplifiers 24-26 each include a digital/analog converter (DAC), which is controlled by a sequence controller 18 for time-accurate generation of gradient pulses.

Located within the gradient field system 3 is a radio-frequency antenna 4 which converts the radio-frequency pulses emitted by a radio-frequency power amplifier into an alternating magnetic field to excite the nuclei and align the nuclear spins of the subject to be examined or, respectively, of the region of the subject that is to be examined. The radio-frequency antenna 4 has one or more RF transmission coils and multiple RF reception coils in the form of an arrangement (annular, linear or matrix-like, for example) of coils. The alternating field emanating from the precessing nuclear spins—normally the nuclear spin echo signals caused by a pulse sequence made up of one or more radio-frequency pulses and one or more gradient pulses—is also transduced by the RF reception coils of the radio-frequency antenna 4 into a voltage (measurement signal) which is supplied via an amplifier 7 to a radio-frequency reception channel 8, 8' of a radio-frequency system 22. The radio-frequency system 22 furthermore has a transmission channel 9 in which the radio-frequency pulses are generated for the excitation of the magnetic resonance signals. The respective radio-frequency pulses are represented digitally in the sequence controller 18 as a series of complex numbers based on a pulse sequence predetermined by the system computer 20. This number series is supplied as real part and imaginary part via respective inputs 12 to a digital/analog converter (DAC) in the radio-frequency system 22, and from this to the transmission channel 9. In the transmission channel 9 the pulse sequences are modulated on a radio-frequency carrier signal whose base frequency corresponds to the resonance frequency of the nuclear spins in the measurement volume. The modulated pulse sequences are supplied to the RF transmission coil of the radio-frequency antenna 4 via an amplifier 28.

The switch-over from transmission operation to reception operation takes place via a transmission/reception diplexer 6. The RF transmission coil of the radio-frequency antenna 4 radiates the radio-frequency pulses into the measurement volume M to excite the nuclear spins and samples resulting echo signals via the RF reception coils. The correspondingly acquired nuclear magnetic resonance signals are phase-sensitively demodulated at an intermediate frequency in a first demodulator 8' of the reception channel of the radio-frequency system 22 and are digitized in the analog/digital converter (ADC). This signal is further demodulated to a frequency of zero. The demodulation to a frequency of zero and the separation into real part and imaginary part occur after the digitization in the digital domain in a second demodulator 8 which outputs the demodulated data via outputs 11 to an image computer 17. An MR image is reconstructed by the image computer 17 from the measurement data acquired in such a manner, in particular using the method according to the invention, which comprises a calculation of at least one perturbation matrix and its inversion (by means of the image computer 17, for example). The administration of the measurement data, the image data and the control programs takes place via the system computer 20. Based on a specification with control programs, the sequence controller 18 controls the generation of the respective desired pulse sequences and the corresponding scanning of k-space. In particular, the sequence controller 18 controls the accurately-timed switching of the gradients, the emission of the radio-frequency pulses with defined phase amplitude, and the reception of the nuclear magnetic resonance signals. The time base for the radio-frequency system 22 and the sequence controller 18 is provided by a synthesizer. The selection of corresponding control programs to generate a series of MR images (which are stored on a DVD 21, for example) as well as other inputs on the part of the user and the presentation of the generated MR images take place via a terminal 13 that has input means (for example a keyboard 15 and/or a mouse 16) to enable an input and display means (a monitor 14, for example) to enable a display.

Figure 3:
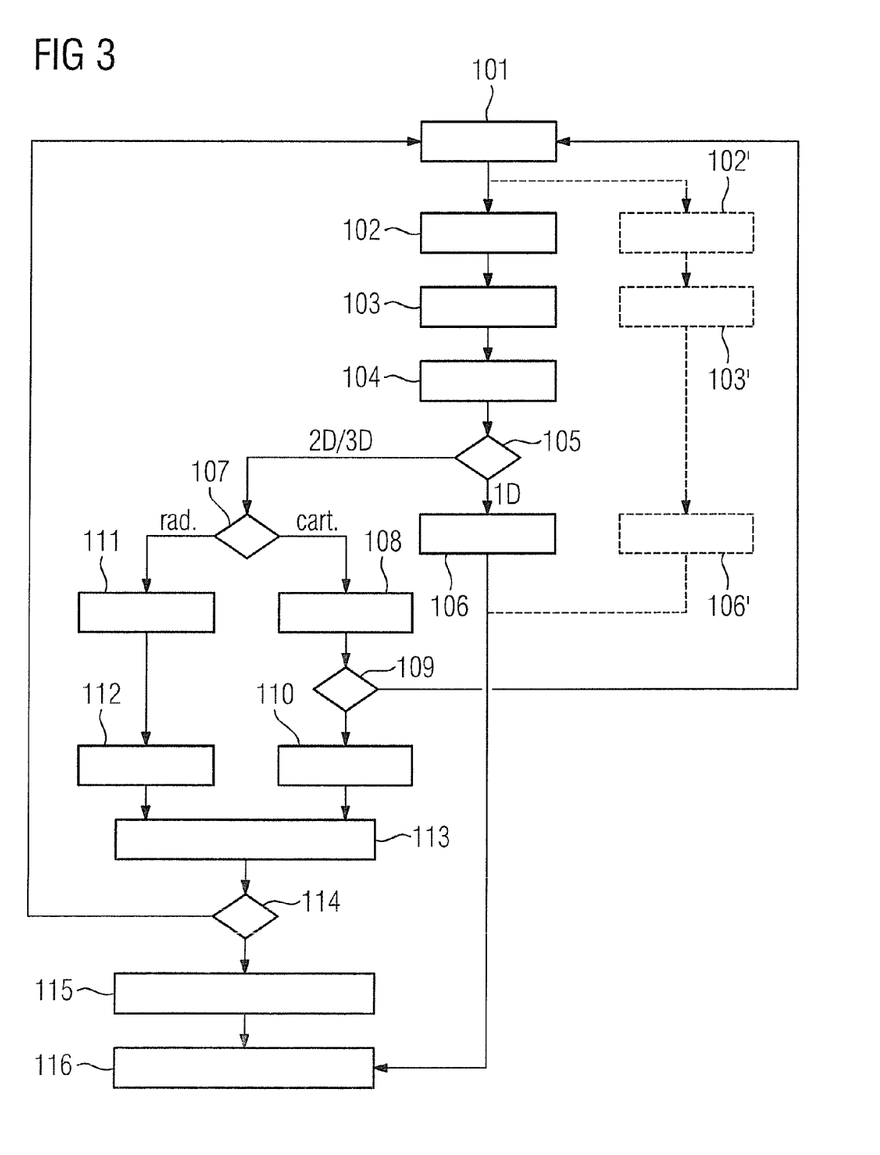
FIG. 3 is a flowchart of an embodiment of the method according to the invention.

A workflow diagram of an example of a method according to the invention is schematically presented in FIG. 3. In the course of an MR measurement, in Step 101 a non-selective excitation pulse is radiated into the subject to be measured while a gradient is switched at the same time. As described above, the excitation is hereby insufficient due to the switched gradients. In an additional step 102, magnetic resonance signals triggered by the insufficient excitation 101 are measured and acquired as measurement data F'(k) in k-space (see Equation (3) above).

A perturbation matrix $D_{kx}$ is calculated (as has likewise already been described above) in a further Step 103 and inverted in Step 104. The inverted perturbation matrix $D_{kx}^{-1}$ is obtained via the matrix inversion of the perturbation matrix $D_{kx}$ in Step 104.

If the MR measurement is a one-dimensional 1D measurement—thus for example a 1D projection of the subject to be measured (Query 105, downward arrow)—in Step 105 the perturbation-free, corrected image I(x) can be calculated with the aid of the inverted perturbation matrix $D_{kx}^{-1}$ and the measured F'(k) using Equation (7) $I(x) = D_{kx}^{-1} F'(k)$. The calculated corrected image can furthermore be displayed and/or be stored for further use, for example on an image computer of the magnetic resonance system (Step 116).

If the MR measurement is a two-dimensional (2D) or three-dimensional (3D) measurement (Query 105, leftward arrow), the workflow can proceed differently depending on the type of acquisition of the measurement data. This is described in the following without limitation of the generality in the example of an MR measurement by means of a PETRA sequence, which acquires part of the measurement data by means of a radial scanning of k-space and part of the measurement data by means of a Cartesian scan of k-space.

In order to keep the matrix sizes and the calculation times as small as possible, it can be reasonable to utilize a present radial symmetry in k-space and, for example, to correct individual radial projections (1D) given radially acquired measurement data, as is described in Steps 101 through 106. Measurement data acquired in a Cartesian manner can be collected and, in larger matrices, can also be corrected in two-dimensional or three-dimensional space depending on the measurement type, as is described further using Steps 101 through 110. The corrected images acquired from the individual measurement parts can ultimately be assembled into a common corrected image via a complex multiplication (see FIG. 4).

It can be reasonable to do this not in image space but rather in k-space. If a Fourier transformation is applied to Equation (7), the following relationship is found between distorted k-space F'(k) or $F'_k$ in matrix notation and undistorted, corrected k-space F(k) or $F_k$ in matrix notation:

$$F_k = E_{kx} D_{kx}^{-1} F'_k. \quad (8)$$

For $E(k,x) = E_{kx}$ it applies that:

$$E_{kx} = e^{ikx}. \quad (9)$$

Using Equation (8), the calculation of a corrected image thus comprises a calculation of an undistorted k-space $F_k$ in which the acquired measurement data are corrected from distorted k-space $F'_k$ in which the measurement data were acquired using the perturbation matrix $D_{kx}^{-1}$ inverted by the matrix inversion.

The workflow can proceed as follows during an MR measurement, for example.

If the measurement data are acquired by means of a Cartesian scanning of k-space (Query 107, rightward arrow "cart."), all measurement points acquired in a Cartesian manner are initially collected bit by bit in a matrix of distorted k-space $F'_{cart}(k)$ that is scanned in a Cartesian manner (Step 108), until all k-space points acquired in a Cartesian manner are excited. In Query 109 a query is made as to whether all k-space points to be acquired have been acquired in the matrix of k-space $F'_{cart}(k)$ that is scanned in a Cartesian manner (Query 109, downward arrow), or whether additional k-space points have yet to be excited (Step 101) and acquired (Step 102) (Query 109, rightward arrow).

If the entirety of k-space $F'_{cart}(k)$ to be scanned in a Cartesian manner has been acquired, undistorted Cartesian k-space $F_{cart}(k) = E_{kx} D_{kx}^{-1} F'_{cart}(k)$ can be calculated by means of Equation (8) (Step 110). Alternatively, a corrected image $I_{cart}(x) = D_{kx}^{-1} F'_{cart}(k)$ can be calculated directly by means of Equation (7) from the entirety of k-space $F'_{cart}(k)$ to be scanned in a Cartesian manner (described in detail further below with regard to FIG. 4). In order to obtain a corrected MR image reflecting all k-space points acquired within the entire MR measurement, such a corrected image $I_{cart}(x)$ would, for example, be to be complexly multiplied, for example as mentioned above with corrected images I(x) obtained according to Steps 101 through 106.

If the measurement data are acquired by means of a radial scan of k-space (Query 107, leftward arrow "rad."), for each radial projection i undistorted radial k-space $F^*_{rad,i}(k) = E_{kx} D_{kx,i}^{-1} F'_{rad,i}(k)$ can respectively be calculated according to Equation (8) (Step 111), instead of a calculation of an undistorted image according to Equation (7) or as in Steps 101 through 106. Since the radially acquired k-space points are for the most part not situated on a Cartesian grid in k-space, in a further Step 112 undistorted radial k-space $F^*_{rad,i}(k)$ can be transferred via what is known as "gridding" or "regridding" to undistorted k-space $F_{rad,i}(k)$ comprising Cartesian k-space points. The Queries 105 and 107 (and 107\*—see FIG. 4) separate the acquired measurement data before the calculation of a corrected image (thus hereby according to the manner in which they were acquired) into groups.

Measurement data converted to undistorted k-spaces $F_{rad,i}(k)$ and $F_{cart}(k)$ in the course of a measurement can be combined in common undistorted k-space F(k). Common undistorted k-space F(k) corresponds to target k-space, which is composed of all excitations and measurements that have taken place.

In Query 114 a query is made as to whether all radial measurements i for the desired 2D or 3D measurements have been implemented, and whether the acquired measurement data have been transferred into common undistorted k-space f(k). If this is not the case (Query 114, leftward arrow), the workflow continues with an additional excitation (Step 101) and acquisition (Step 102) of measurement data to be acquired radially, until all desired measurement data have been acquired (Query 114, downward arrow). In the latter case, a corrected image can now be calculated from completely filled common undistorted k-space F(k) (Step 115), which corrected image can be displayed in Step 116 and/or be stored for further use.

If the acquisition of the measurement data after an excitation 101 takes place via full radial projections, and if the dependency of k in the excitation profile P(k,x) in Equation (3) is therefore omitted, the excitation profile is only a function of the location x, i.e. P(k,x) = P(x); Equation (3) corresponds to a convolution of k-space with P(x). Such a perturbation can be remedied simply in that distorted k-space $F_x'(k)$ is brought into a distorted image space $I_x'(x)$ (image domain) via Fourier back-transformation (analogous to Equation (2)). The relationship $$I_x(x) = \frac{I_x'(x)}{P(x)}. \quad (10)$$

then exists between the undistorted image space $I_x(x)$ and distorted image space $I_x'(x)$. The undistorted image $I_x(x)$ can therefore be calculated by division of the distorted image $I_x'(x)$ by the excitation profile P(x) that is not dependent on the k-space point.

For example, given a PETRA sequence such an acquisition of measurement data can take place after an excitation pulse. For example, given acquisition of measurement data at a second echo time after acquisition of measurement data after a first ultrashort echo time [sic]. For example, the measurement data acquired at Step 102' can thus be converted—by means of a perturbation calculated in Step 103' in the form of the excitation profile P(x)—directly into undistorted images $I_x(x)$ by means of Equation (10) specified above, and can likewise be displayed in Step 116 and/or be stored for further use.

Figure 4:
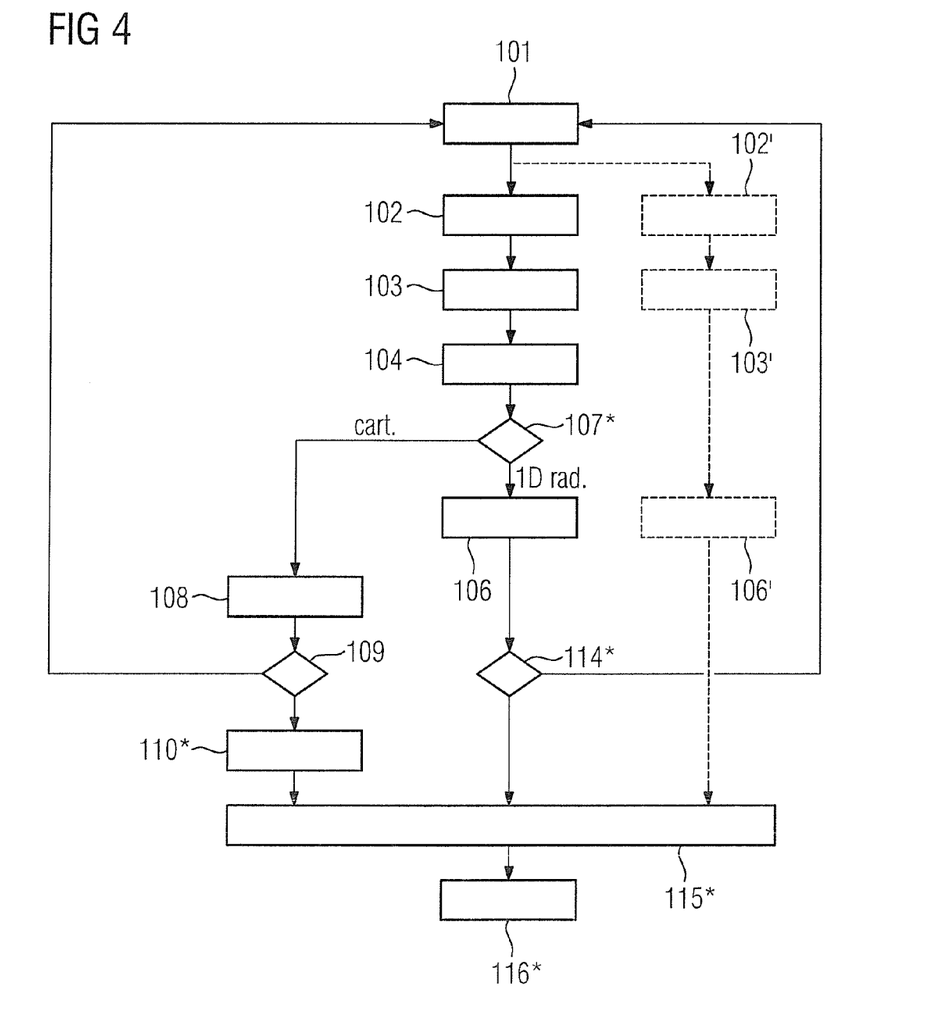
FIG. 4 is a flowchart of a further embodiment of the method according to the invention.

In a further schematic workflow diagram, FIG. 4 illustrates an additional exemplary embodiment of a method according to the invention in which (as was already mentioned above) corrected images obtained from the individual measurement parts are combined into a common corrected image via complex multiplication. The workflow initially corresponds to the workflow of FIG. 3, so the same steps are designated with the same reference characters.

Given a one-dimensional (1D) scanning of k-space, for example a radial projection, as described in FIG. 3 an undistorted image $I(x)=D_{kx}^{-1}F'(k)$ is calculated in Step 106 using Equation (7), wherein here the query 107\* is made as to whether the measurement data have been scanned one-dimensionally, for example in a radial projection (Query 107\*, downward arrow, "1D rad.") or in a Cartesian manner (Query 107\*, leftward arrow, "cart.").

If multiple one-dimensional scans j take place in the course of the measurement, an undistorted image $I_j(x)=D_{kx,j}^{-1}F_j'(k)$ is calculated in Step 106 for each of these scans. The Query 114 is made as to whether all such one-dimensional scans have taken place and associated corrected images have been calculated (Query 114\*, downward arrow) or not (Query 114\*, rightward arrow), after which the workflow begins again with an excitation 101.

Given a Cartesian scanning of k-space, it is not undistorted k-space $F_{cart}(k)=E_{kx}D_{kx}^{-1}F'_{cart}(k)$ that is calculated according to Equation (8), as in Step 110 from FIG. 3; rather, in Step 110\* a corrected image $I_{cart}(x)=D_{kx}^{-1}F'_{cart}(k)$ is calculated according to Equation (7).

As described with reference to FIG. 3, an undistorted image $I_x(x)$ is also possibly calculated in Step 106' [sic] acquired measurement data in which the excitation profile depends only on the location x (Steps 101, 102', 103' and 106').

The respective calculated, undistorted images $I_{cart}(x)$, $I_j(x)$ and possibly $I_x(x)$ are processed in Step 115\* via complex multiplication into a complete undistorted image I(x) which can be displayed and/or stored for additional processing in Step 116\*. Depending on the application, the undistorted images $I_x(x)$ from Step 106' can also be additionally offset against the complete undistorted image I(x) to calculate difference images or the like.

In both the exemplary embodiment described using FIG. 3 and the exemplary embodiment described using FIG. 4, calculated corrected images and/or additional calculated uncorrected images (calculated according to Equation (4)) can also be arbitrarily combined into intermediate images, for example respectively within the group of measurement data acquired in a Cartesian manner and within the group of radially acquired measurement data. For example, according to one of the exemplary embodiments shown using FIG. 3 or FIG. 4 only specific radial projections can be corrected (as corrected images $I_{rad,t}(x)$ and/or as corrected k-spaces $F_{rad,t}(k)$) in order to save calculation time, and these corrected projections can be combined with uncorrected [sic] (in which, for example, only a slight perturbation is to be expected due to only weakly switched gradients) into a common corrected image I(x). Analogously, only specific measurement points acquired in a Cartesian manner can also be acquired in corrected k-space $F_{cart}(k)$ in which additional uncorrected measurement values are acquired in which only a slight perturbation is again expected.

The embodiments described using FIG. 3 and FIG. 4 can also be combined in order to calculate a common corrected image I(x). For example, selection of measurement data acquired as radial projections and/or a selection of measurement data acquired in a Cartesian manner can be acquired by a method according to FIG. 3 in Step 113 in target k-space, from which a corrected image is calculated which is in turn offset (via complex multiplication) against corrected images (calculated according to the method described using FIG. 4) to form a common corrected image.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for correction of artifacts in magnetic resonance (MR) resonance images, comprising:
    entering MR measurement data, acquired with a pulse sequence in which gradients are activated simultaneously during radiation of at least one non-selective excitation pulse, into a memory representing k-space;
    from a processor, accessing said MR measurement data in said k-space memory and, in said processor, determining a perturbation matrix on spatial data of the acquired MR measurement data, and said measurement data in k-space, and the gradients used in said sequence;
    in said processor, inverting said perturbation matrix to obtain an inverted perturbation matrix, and calculating a corrected image from the MR measurement data in k-space and the inverted perturbation matrix by a matrix multiplication of said inverted perturbation matrix with said MR measurement data in k-space; and
    making said corrected image available as a data file at an output of said processor.

2. A method as claimed in claim 1 comprising determining said perturbation matrix based on an excitation profile of said at least one non-selected excitation pulse.

3. A method as claimed in claim 1 comprising separating said MR measurement data in k-space into a plurality of groups before calculating said corrected image, dependent on acquisition of the respective groups.

4. A method as claimed in claim 3 comprising calculating said corrected image as a collection of all MR measurement data acquired in a Cartesian manner in a matrix of distorted k-space, scanned in said Cartesian manner.

5. A method as claimed in claim 3 comprising calculating said corrected image as a separate calculation of a corrected image or corrected k-space for MR measurement data acquired as a one-dimensional projection.

6. A method as claimed in claim 1 comprising separating said MR measurement data into a plurality of groups before calculating said corrected image, dependent on a manner by which said MR measurement data were acquired in said sequence and, for each group, calculating undistorted k-space using said inverted perturbation matrix, thereby obtaining a plurality of undistorted k-spaces for the respective groups, and combining said plurality undistorted k-spaces into a common undistorted k-space.

7. A method as claimed in claim 1 comprising separating the acquired MR measurement data into groups before calculating said corrected image, dependent on a manner by which the respective groups were acquired in said sequence, and, for each group, calculating a corrected image, thereby obtaining a plurality of corrected images for the respective groups, and calculating a common corrected image from said plurality of corrected images by complex multiplication.

8. A method as claimed in claim 1 wherein said MR measurement data include data dependent on an excitation profile of said non-selective excitation pulse, and, in said processor, calculating an additional corrected image by dividing respective pixels of a distorted image by said excitation profile.

9. A method as claimed in claim 8 comprising, in said processor, calculating a difference image and said corrected image and said additional corrected image, and making said difference image available at an output of said processor as a further data file.

10. A magnetic resonance (MR) apparatus, comprising:
an MR data acquisition unit;
a control unit configured to operate said MR data acquisition unit to acquire MR measurement data with a pulse sequence in which gradients are activated simultaneously during radiation of at least one non-selective excitation pulse, and to enter said MR measurement data into a memory representing k-space;
a processor configured to access said MR measurement data in said k-space memory and determine a perturbation matrix based on spatial data of the acquired MR measurement data, and said measurement data in k-space, and the gradients used in said sequence;
said processor being configured to invert said perturbation matrix to obtain an inverted perturbation matrix, and to calculate a corrected image from the MR measurement data in k-space and the inverted perturbation matrix by a matrix multiplication of said inverted perturbation matrix with said MR measurement data in k-space; and
said processor being configured to make said corrected image available as a data file at an output of said processor.

11. A non-transitory, computer-readable data storage medium encoded with programming instructions that, when said storage medium is loaded into a computerized processor, cause said computerized processor to:
operate said MR data acquisition unit to acquire MR measurement data with a pulse sequence in which gradients are activated simultaneously during radiation of at least one non-selective excitation pulse, and to enter said MR measurement data into a memory representing k-space;
access said MR measurement data in said k-space memory and determine a perturbation matrix based on spatial data of the acquired MR measurement data, and said measurement data in k-space, and the gradients used in said sequence;
invert said perturbation matrix to obtain an inverted perturbation matrix, and calculate a corrected image from the MR measurement data in k-space and the inverted perturbation matrix by a matrix multiplication of said inverted perturbation matrix with said MR measurement data in k-space; and
make said corrected image available as a data file.

* * * * *